United States Patent [19]
Koch et al.

[11] 4,005,159
[45] Jan. 25, 1977

[54] HYDROXY CONTAINING PHOSPHONATES

[75] Inventors: Frederick William Koch, Willoughby Hills; Jerry Lee Musser, Chardon, both of Ohio

[73] Assignee: The Lubrizol Corporation, Cleveland, Ohio

[22] Filed: Aug. 5, 1975

[21] Appl. No.: 602,036

Related U.S. Application Data

[63] Continuation-in-part of Ser. No. 403,373, Oct. 4, 1973, Pat. No. 3,932,290.

[52] U.S. Cl. .............................. 260/953; 252/49.8; 260/970
[51] Int. Cl.$^2$ .......................................... C07F 9/40
[58] Field of Search ........................... 260/953, 970

[56] References Cited

OTHER PUBLICATIONS

Kreutzkamp, "Naturwissenschaften," 43, pp. 81–82 (1956).

*Primary Examiner*—Anton H. Sutto
*Attorney, Agent, or Firm*—James W. Adams, Jr.; William H. Pittman

[57] ABSTRACT

Compositions prepared by the reaction of a di-(lower alkyl) phosphite with a $C_{10-20}$ epoxide in the presence of a strongly alkaline reagent are useful as friction-reducing additives in functional fluids, especially automatic transmission fluids.

8 Claims, No Drawings

HYDROXY CONTAINING PHOSPHONATES

This application is a continuation-in-part of copending application Ser. No. 403,373, filed Oct. 4, 1973, now U.S. Pat. No. 3,932,290.

This invention relates to new compositions of matter suitable for use as friction reducing additives in functional fluids, and to functional fluids containing the same. More particularly, it relates to compositions prepared by reacting at least one phosphorus compound of the formula

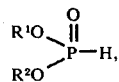

wherein each of $R^1$ and $R^2$ is a lower alkyl-based radical, with at least one epoxide of the formula

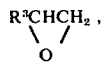

wherein $R^3$ is an alkyl radical having 10–20 carbon atoms.

The development of functional fluids for power transmission, including such materials as hydraulic fluids and automatic transmission fluids, has necessitated the development of new additives to improve power transmission properties. One of the properties which must frequently be changed is the frictional nature of the liquid. Thus, it is sometimes preferred that the fluid have a coefficient of friction substantially lower than that of the base oil which is its major component. Improved friction-reducing additives have therefore been of considerable interest.

A principal object of the present invention, therefore, is to produce new phosphorus-containing compositions of matter.

A further object is to produce compositions which decrease the coefficient of friction of a functional fluid when incorporated therein.

Another object is to provide new fluids suitable for power transmission, especially in automatic transmissions.

Still another object is to provide automatic transmission fluids and other functional fluids having a low coefficient of friction.

Other objects will in part be obvious and will in part appear hereinafter.

As previously indicated, the compositions of this invention are prepared by the reaction of a phosphite diester with an epoxide. The phosphite diester has the formula given hereinabove wherein each of $R^1$ and $R^2$ is a lower alkyl-based radical and usually a lower alkyl radical.

As used herein, the term "lower alkyl-based radical" denotes a radical having not more than 7 carbon atoms, having a carbon atom directly attached to the remainder of the molecule (i.e., to the phosphorus atom) and having predominantly alkyl character within the context of this invention. Such radicals include the following:

1. Lower alkyl radicals; that is, methyl, ethyl, propyl, butyl, pentyl, hexyl or heptyl radicals (all isomers being included).

2. Substituted lower alkyl radicals; that is, radicals containing non-hydrocarbon substituents which, in the context of this invention, do not alter the predominantly alkyl character of the radical. Those skilled in the art will be aware of suitable substituents; examples include halide, nitro, hydroxy,

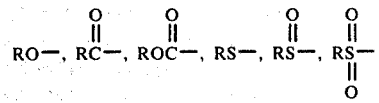

(R being a hydrocarbon radical and usually a lower alkyl radical).

3. Hetero radicals; that is, radicals which, while predominantly alkyl in character within the context of this invention, contain atoms other than carbon present in a chain or ring otherwise composed of carbon atoms. Suitable hetero atoms will be apparent to those skilled in the art and include, for example, oxygen, nitrogen and sulfur.

In general, no more than about one substituent or hetero atom will be present in the lower alkyl-based radical.

The epoxide is one which contains about 12–22 carbon atoms, such as dodecylene oxide, pentadecylene oxide or eicosene oxide (all isomers being included). Epoxides derived from straight-chain α-olefins are preferred. Commercial mixtures of such epoxides are available and their use is contemplated as part of this invention.

The proportions of the two reactants are not critical, since any excess of either reactant will merely remain in the product without substantially affecting its properties. It is usually preferred to use approximately equimolar amounts of the two, or a slight excess of the epoxide; for example, about 1.0–1.5 moles of the epoxide per mole of dialkyl phosphite.

The reaction is carried out in the presence of a strongly alkaline reagent, usually an alkali metal or an alkyl, alkoxide, amide or the like derived therefrom. A very small amount of alkaline reagent is generally needed, usually about 0.01–0.5% based on the total weight of the reactants.

The reaction is carried out by merely heating the mixture to a temperature above about 100° C. and below the decomposition temperature thereof, generally about 150°–225° C. It is preferably effected in an atmosphere of an inert gas such as nitrogen. Inert diluents may be used but are usually not necessary.

Following the reaction, volatiles may be removed as by stripping, usually under vacuum, and the residue is filtered to afford the desired product. If necessary, the product may be purified by conventional means, but it is usually possible to employ it for the purposes of this invention without purification.

The compositions of this invention are probably mixtures rather than simple chemical compounds, and thus it is possible to define them completely only in terms of the method for their preparation. However, there is evidence that the reaction between the phosphite and the epoxide is chiefly a simple addition reaction and that the predominant product has the formula

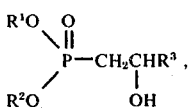

wherein $R^1$, $R^2$ and $R^3$ are as previously defined. Compounds of this formula may be separated from other materials present in the product by conventional separation means such as chromatography, and such compounds are contemplated as part of this invention.

The preparation of the compositions of this invention is illustrated by the following examples. All parts and percentages are by weight.

EXAMPLE 1

A mixture of 194 parts (1 mole) of di-n-butyl phosphite, 239 parts (1 mole) of an epoxide derived from a commercial mixture of $C_{14}$ and $C_{16}$ straight chain α-olefins, and 0.2 part of sodium methoxide is heated for eight hours at 190°–200° C. An additional 60 parts (0.25 mole) of epoxide are added and heating is continued at 200°–205° C. for eight hours. Volatile materials are then removed by vacuum stripping at 150° C. and the residue is filtered through a filter aid material to yield the desired product which contains 6.28% phosphorus.

EXAMPLE 2

A mixture of 776 parts (4 moles) of di-n-butyl phosphite and 1195 parts (5 moles) of the epoxide of Example 1 is purged with nitrogen, and 4.6 parts of sodium metal is added. The mixture is heated at 160°–170° C. for ten hours under nitrogen, and is then filtered through a filter aid material. The filtrate, which is the desired product, contains 6.30% phosphorus.

EXAMPLE 3

The procedure of Example 2 is repeated, except that di-isohexyl phosphite is substituted on an equimolar basis for the di-n-butyl phosphite. A similar product is obtained.

EXAMPLE 4

The procedure of Example 2 is repeated, except that the epoxide used is an epoxide derived from propene tetramer. A similar product is obtained.

As previously indicated, the composition of this invention are useful as friction-modifying additives in functional fluids. As such, they can be employed in a variety of fluids based on diverse oils of lubricating viscosity, including natural and synthetic lubricating oils and mixtures thereof. The fluids contemplated include principally automatic transmission fluids, transaxle lubricants, hydraulic fluids and the like, but other lubricating oil and grease compositions can also benefit from the incorporation of the present compositions.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halosubstituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes), etc. and mixtures thereof]; alkylbenzenes (e.g., dodecylbenzenes, tetradecylbenzenes, dinonylbenzenes, di-(2-ethylhexyl)-benzenes, etc.); polyphenyls (e.g., biphenyls, terphenyls, alkylated polyphenyls, etc.), alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500—1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl) silicate, tetra-(4-methyl-2-ethylhexyl) silicate, tetra-(p-tert-butylphenyl) silicate, hexyl-(4-methyl-2-pentoxy)-disiloxane, poly(methyl)-siloxanes, poly(methylphenyl)siloxanes, etc.). Other synthetic lubricating oils include liquid esters of phosphorus-containing acids (e.g., tricresyl phosphate, trioctyl phosphate, diethyl ester of decylphosphonic acid, etc.), polymeric tetrahydrofurans and the like.

Unrefined, refined and rerefined oils (and mixtures of each with each other) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

In general, about 0.05–20.0 parts (by weight) of the composition of this invention is dissolved in 100 parts of oil to produce a satisfactory fluid. The invention also contemplates the use of other additives in combination with the products of this invention. Such additives include, for example, detergents and dispersants of the ash-containing or ashless type, oxidation inhibiting agents, pour point depressing agents, extreme pressure agents, color stabilizers and anti-foam agents.

The ash-containing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-$\beta$-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are illustrated by the interpolymers of an oil-solubilizing monomer, e.g., decyl methacrylate, vinyl decyl ether, or high molecular weight olefin, with a monomer containing polar substituents, e.g., aminoalkyl acrylate or poly-(oxyethylene)-substituted acrylate; the amine salts, amides, and imides of oil-soluble monocarboxylic or dicarboxylic acids such as stearic acid, oleic acid, tall oil acid, and high molecular weight alkyl or alkenyl-substituted succinic acid. Especially useful as ashless detergents are the acylated polyamines and similar nitrogen compounds containing at least about 54 carbon atoms as described in U.S. Pat. No. 3,272,746; reaction products of such compounds with other reagents including boron compounds, phosphorus compounds, epoxides, aldehydes, organic acids and the like; and esters of hydrocarbon-substituted succinic acids as described in U.S. Pat. No. 3,381,022.

Auxiliary extreme pressure agents and corrosion-inhibiting and oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentyl phenyl phosphite, dipentyl phenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)-phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

It is possible to form the functional fluids of this invention by dissolving the various additives, or oil solutions thereof, directly in an oil. However, it is often more convenient to prepare additive concentrates containing the composition of this invention in amounts of about 20–90% by weight, optionally in combination with one or more of the other additives described hereinabove, the balance of said concentrates being a substantially inert, normally liquid diluent such as mineral oil, and to dissolve these concentrates in the oil to form the functional fluid.

A typical automatic transmission fluid of this invention has the following composition, all percentages being by weight:

| | |
|---|---|
| Mineral oil (ATF base) | 92.25% |
| Product of Example 1 | 0.13% |
| Polyisobutenyl succinic anhydride-polyethylene polyamine (3–7 amino groups) reaction product | 1.75% |
| Reaction product of boric acid with polyisobutenyl succinic anhydride-polyethylene polyamine reaction product | 0.67% |
| Zinc di-(isooctyl)phosphorodithioate | 0.64% |
| Tallow-substituted diethanolamine | 0.10% |
| Mixed ester-amide of maleic anhydride-styrene copolymer (12% soln. in toluene) | 1.20% |
| Hydrocarbon resin seal swelling agent | 3.00% |
| Substituted diphenylamine | 0.20% |
| Reaction product of glycidol (2 moles) with $C_{12}$ primary amine mixture (1 mole) | 0.04% |
| Silicone anti-foam agent | 0.02% |

What is claimed is:

1. A composition of matter prepared by reacting at least one phosphorus compound of the formula

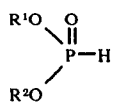

wherein each of $R^1$ and $R^2$ is a lower alkyl-based radical, with at least one epoxide of the formula

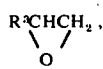

wherein $R^3$ is an alkyl radical having 10–20 carbon atoms.

2. A composition according to claim 1 wherein each of $R^1$ and $R^2$ is a lower alkyl radical.

3. A composition according to claim 2 wherein the epoxide is derived from a commercial mixture of $C_{14}$ and $C_{16}$ straight chain α-olefins.

4. A composition according to claim 3 wherein $R^1$ and $R^2$ are n-butyl radicals.

5. A composition of matter consisting essentially of at least one compound of the formula

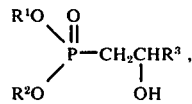

wherein each of $R^1$ and $R^2$ is a lower alkyl-based radical and $R^3$ is an alkyl radical having 10–20 carbon atoms.

6. A composition according to claim 5 wherein each of $R^1$ and $R^2$ is a lower alkyl radical.

7. A composition according to claim 6 wherein $R^3$ is a mixture of $C_{12}$ and $C_{14}$ straight chain alkyl groups.

8. A composition according to claim 7 wherein $R^1$ and $R^2$ are n-butyl radicals.

* * * * *